United States Patent
Cazal

(10) Patent No.: US 11,864,840 B2
(45) Date of Patent: Jan. 9, 2024

(54) METHOD AND DEVICE FOR ASSISTING A SURGEON FIT A PROSTHESIS, IN PARTICULAR A HIP PROSTHESIS, FOLLOWING DIFFERENT SURGICAL PROTOCOLS

(71) Applicant: Laurent Cazal, Limoges (FR)

(72) Inventor: Laurent Cazal, Limoges (FR)

( * ) Notice: Subject to any disclaimer, the term of this patent is extended or adjusted under 35 U.S.C. 154(b) by 1033 days.

(21) Appl. No.: 16/482,556

(22) PCT Filed: Jan. 31, 2018

(86) PCT No.: PCT/EP2018/052388
§ 371 (c)(1),
(2) Date: Jul. 31, 2019

(87) PCT Pub. No.: WO2018/141787
PCT Pub. Date: Aug. 9, 2018

(65) Prior Publication Data
US 2020/0000527 A1    Jan. 2, 2020

(30) Foreign Application Priority Data
Feb. 1, 2017  (FR) ...................................... 1770103

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/361* (2016.02); *A61B 90/39* (2016.02);
(Continued)

(58) Field of Classification Search
CPC ....... A61B 34/20; A61B 34/25; A61B 90/361; A61B 90/39; A61B 2034/105; A61B 2090/365; A61B 2090/3916; A61B 2090/3937; A61B 2090/3983; A61B 2562/0219; A61B 2562/0223; G06T 7/74;
(Continued)

(56) References Cited

U.S. PATENT DOCUMENTS

2012/0157887 A1* 6/2012 Fanson ..................... A61F 2/46
600/595
2014/0005531 A1* 1/2014 Taylor ..................... A61B 5/06
600/424
(Continued)

FOREIGN PATENT DOCUMENTS

WO    2012084739 A1    6/2012
WO    2015164402 A1    10/2015

OTHER PUBLICATIONS

International Search Report; priority document.

*Primary Examiner* — Zade Coley
*Assistant Examiner* — Diana Jones
(74) *Attorney, Agent, or Firm* — Greer, Burns & Crain, Ltd.

(57) ABSTRACT

A method and a device for helping a surgeon during the application of a determined and known orthopedic surgery protocol, comprising steps of overlaying determined and recorded virtual data, based on 3D markers, so as to allow the surgeon to continuously overlay the virtual spatial information with the actual data of the limbs of the patient.

5 Claims, 4 Drawing Sheets

(51) Int. Cl.
*A61B 90/00* (2016.01)
*G06T 7/73* (2017.01)
*G06K 19/06* (2006.01)
*A61B 34/10* (2016.01)
*A61F 2/46* (2006.01)

(52) U.S. Cl.
CPC .......... *G06K 19/06037* (2013.01); *G06T 7/74* (2017.01); *A61B 2034/105* (2016.02); *A61B 2090/365* (2016.02); *A61B 2090/3916* (2016.02); *A61B 2090/3937* (2016.02); *A61B 2090/3983* (2016.02); *A61B 2562/0219* (2013.01); *A61B 2562/0223* (2013.01); *A61F 2/4684* (2013.01); *A61F 2002/4633* (2013.01); *G06T 2207/30008* (2013.01); *G06T 2207/30204* (2013.01)

(58) Field of Classification Search
CPC .......... G06T 2207/30008; G06T 2207/30204; G06K 19/06037; A61F 2/4684; A61F 2002/4633
See application file for complete search history.

(56) References Cited

U.S. PATENT DOCUMENTS

| | | | |
|---|---|---|---|
| 2014/0039527 A1* | 2/2014 | Avelar | A61B 17/06166 606/144 |
| 2016/0143699 A1* | 5/2016 | Tanji | A61B 34/20 600/431 |
| 2017/0028178 A1* | 2/2017 | Skoda | A61B 5/4064 |
| 2017/0042631 A1* | 2/2017 | Doo | H04N 13/398 |

* cited by examiner

METHOD AND DEVICE FOR ASSISTING A SURGEON FIT A PROSTHESIS, IN PARTICULAR A HIP PROSTHESIS, FOLLOWING DIFFERENT SURGICAL PROTOCOLS

CROSS-REFERENCES TO RELATED APPLICATIONS

This application claims the benefit of the International Application No. PCT/EP2018/052388, filed on Jan. 31, 2018, and of the French patent application No. 1770103 filed on Feb. 1, 2017, the entire disclosures of which are incorporated herein by way of reference.

FIELD OF THE INVENTION

This invention relates to a method and a device for assisting a surgeon fit a prosthesis, in particular a hip prosthesis, following different orthopedic surgical protocols.

BACKGROUND OF THE INVENTION

Interventions on joints, in particular, are numerous and common. There are different protocols and different approaches, but the method according to this invention is applicable regardless of the chosen protocol and whatever the orthopedic intervention.

There is thus an approach with dislocation before resection of the head, which is the one chosen for this description.

There are other approaches including the so-called anterior approach where the resection is performed in situ, the joint not being dislocated. The surgical steps are different; however, the method and device are perfectly applicable.

Thus, if focusing, for example, on hip arthroplasty, which involves replacing the entire joint with a condylar prosthesis on the pelvic side and a femoral prosthesis on the femur side, it is known that this operation is common.

It takes place in two stages, preoperative and surgical, with follow-up throughout the procedure using the method according to this invention, followed by a third stage consisting of a check-up visit.

The first preoperative step makes it possible to confirm the need for the intervention, to define a range of prostheses suitable for being fitted, with the final decision being taken during the intervention and to confirm a priori the impacted areas.

Disabling osteoarthritis is a common indication for arthroplasty.

Prostheses have made progress both for the acetabular part as well as for the femoral prosthesis part and the ancillary equipment has also been greatly improved.

Surgical protocols are also perfectly defined, as are rehabilitation protocols.

Nevertheless, the intervention is largely left to the dexterity and skills of the surgeon and his/her experience.

Whatever the type of orthopedic intervention, whatever the protocol used, the surgeon must resect at least one bony part, fit at least one prosthesis in the stead and place of the resected part and reposition the prosthesis in a functional manner. In the stead and place of a resection, it is possible that the intervention comprises a resurfacing of the part concerned. Spatial identification requirements remain the same and the method with its accompanying device can find application in both cases.

Indeed, the surgeon works in 3 dimensions because the positions of the different natural or artificial parts are spatially positioned.

In the case of arthroplasty, which is the case of the example given, it becomes even more complex because there is, for example, a resection of the femur head and resurfacing of the acetabulum. In all cases, the surgeon needs to spatially locate themselves to determine the depths and profiles to be achieved while also knowing just how far he/she must go so that the two prosthetic parts can cooperate with each other under the same conditions as before the intervention.

Despite all the existing protocols, in spite of the ancillary materials used, the result of such an intervention can lead to problems of length of the modified lower limb, forcing the patient to compensate using orthopedic insoles.

There can also be angular orientation shifts in abduction or anteversion leading to more limited movement amplitudes and therefore to a deterioration of walking quality.

Observance of the offset is likewise a very important condition so as to not disturb the biomechanics of the limb operated on. This observance is all the more important as the adjacent muscles and tissue envelopes are directly involved.

Similarly, if the surgeon notes a greater degradation of a bony part leading the surgeon to modify the planned protocol, for example, after resection of a bony part, it becomes difficult for the surgeon to be able to locate themselves, this as regards offset, length and orientation.

It is necessary to heed the final length of the lower limb because if there is a difference in length of greater than 1 cm between the two lower limbs, then the patient will feel assured discomfort, not to mention asymmetries of strain while walking, which can bring about premature wear of the prostheses and/or compensations generating morphoskeletal disorders.

In the context of such assistance during interventions, the prior art patent application US 2012157887 describes a device with implanted sensors to allow surgical measurements with respect to the patient's anatomy, during the intervention.

Thus, a master sensor, provided with optical means, is implanted on the skeleton of the patient, on the pelvis in the case of an intervention on the hip, and a prosthesis template trial gauge is also provided with optical means. One is a transmitter and the other is a receiver for proper alignment and positioning. One of the sensors also includes an inertial guidance unit to improve angular positioning.

A unit with processor and software ensures processing of the optical and inertial information received to display visual information on a medium.

Each sensor works by optical beam and has an internal source for operation, rechargeable, wired, or any other solution being considered.

Such sensors are large and need to be adjusted to check alignments.

The use of the device remains complex.

There are arrangements with passive sensors, which return a signal, for example of the optical type, and a camera deduces the position of the sensor concerned.

These methods do not allow the surgeon to virtually, directly and continuously visualize the movements, the positioning of the various elements during the course of the intervention, overlaid on relevant parts of the patient.

SUMMARY OF THE INVENTION

The method according to this invention aims to use augmented reality to allow direct overlaying of a virtual image displayed by a viewing means such as augmented reality glasses, on a view of a real shape in motion. In such instances, the aim is to position the actual shape with the prostheses in the same configuration as the stored virtual shape, either in the form of reference points or in complete form in the case of complete virtual images, with dimensional information in real time.

The method according to this invention makes it possible to calculate the differentials between real and virtual of at least one prosthesis with respect to the bone that receives it and to allow relative positioning of each of the at least one prosthesis with respect to another bone or to another prosthesis.

For the rest of the description, the application chosen is that of a total hip arthroplasty, with a protocol with prior dislocation and posterior resection, because it involves two prostheses each to position, as regards dimensions and orientation, relative to the bone which receives it, which is to say the pelvis on the one hand and the femur on the other hand, so as to allow a suitable positioning between the two prostheses, amongst themselves.

Thus:

the condylar prosthesis must heed limited angular ranges of abduction and anteversion, as well as also an implant depth so that the center of rotation after the intervention remains unchanged or is in the immediate vicinity of the natural center of rotation before the intervention.

The femoral prosthesis must heed a femoral penetration that is suitable, after the intervention, for allowing overlaying of the center of rotation of the femoral head of the prosthesis with the center of rotation of the condylar prosthesis and therefore with the initial center of rotation before the intervention, so that the conjunction of these positions lead to respect of the length of the lower limb and respect of the offset.

Current methods are complex to implement and require calculations, measurements and notwithstanding all precautions being taken, the most common problem remains that of the difference in length of the lower limb after the intervention relative to the lower limb before the intervention.

The parameters involved in this problem are numerous, a hollowing out that is not suitable for the integration of the condylar prosthesis, impingement of the femoral prosthesis in the femur, orientations of the prosthetic elements and offset of the limb operated on. Besides, any assistance and any practical help is a sign of progress provided that this assistance is provided without disturbing the intervention area, is natural for the practitioner who does not have to perform movements that are different from those normally carried out, all without discomfort and leaving the practitioner completely free in his/her movements.

This invention aims to provide the solutions and to solve the problems of the prior art processes that are unnatural, that disrupt interventions, that are cumbersome and hinder the operation area, that are artificial in their use.

BRIEF DESCRIPTION OF THE DRAWINGS

The method is now described with regard to hip arthroplasty, this by way of example only, without it being considered as limiting. This description is set forth with reference to the accompanying drawings which are shown on the bony parts, which are shown schematically so as not to clutter up the figures. The figures of the drawings show.

DETAILED DESCRIPTION OF THE PREFERRED EMBODIMENTS

Figures 1, 2:
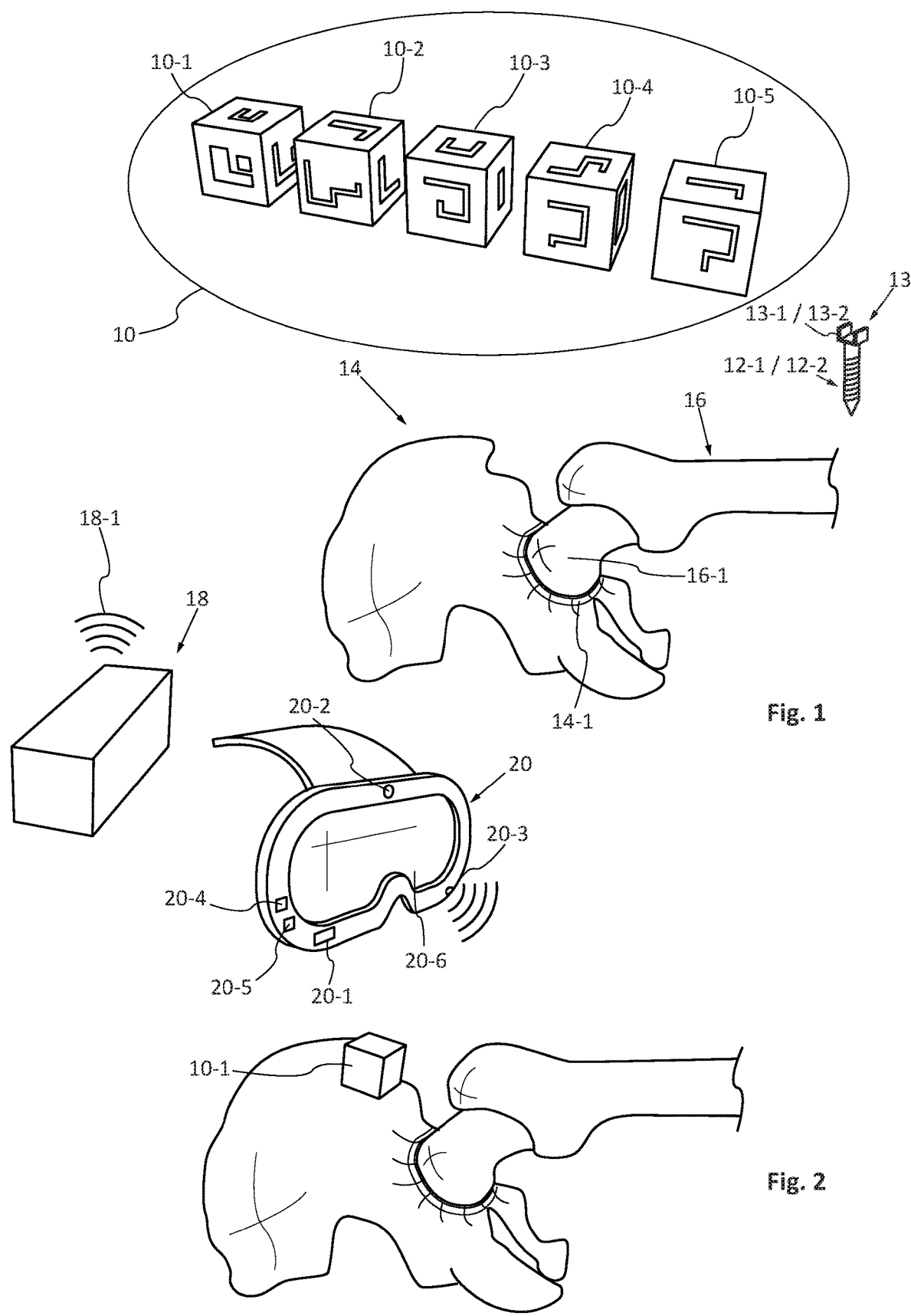
FIG. 1: a view of the device for implementing the method as a whole.
FIG. 2: fitting of a first marker on the pelvis.

FIG. 1 shows the device according to this invention comprising markers 10, in the case in point, a Total Hip Prosthesis intervention, THP, 10-1 to 10-5.

The markers are as follows:

10-1: reference marker associated with the femur,
10-2: reference marker associated with the pelvis,
10-3: marker associated with the femoral head,
10-4: marker associated with the acetabulum, and
10-5: verification marker associated with the trial femoral prosthesis.

In the embodiment chosen, these markers are 3D QR codes, which is to say cubes with each of the faces of each cube being identified by a code and spatially detectable.

These markers 10 are suitable for surgery and can be sterilized and affixed by any means.

Other types of markers could be used provided they can be detected in 3D.

FIG. 1 shows means 12 for attaching these QR code markers to the bony part, for example using a surgical screw 12-1 and 12-2 respectively for the markers 10-1 and 10-2, each of the screws being provided at its free end with means 13, in this case 13-1, 13-2, for snap-fitting the marker in a single position, particularly in orientation. For the other markers, they can be directly applied on the prosthesis as will be described further.

The pelvis 14 and the top of the femur 16 of the patient are schematically shown in FIG. 1.

The acetabulum at 14-1 and the femoral head at 16-1, which are shown healthy, have been detected before dislocation, ignoring, for this description, any areas affected by any disease.

The patient is lying on their side on the operating table in a horizontal lateral decubitus position, which makes it possible to define:

a sagittal plane PS, that is horizontal and parallel to the ground, a transverse plane PT, which is to say, vertical parallel to the ground, perpendicular to the longitudinal axis of the patient, and a frontal plane PF, that is vertical and perpendicular to the sagittal and frontal planes.

Thus, it is possible to define three axes X, Y and Z forming an orthonormal coordinate system, these three axes being included in the three previously indicated planes with an origin O considered to be the marker 10-2 associated with the reference pelvis.

A data processing and recording unit 18 is furthermore provided, this unit is equipped with a means 18-1, of the Bluetooth® type, for short-range exchange with at least one augmented reality mask 20 to be worn by the surgeon during the intervention. The mask may take the form of glasses or a helmet, this being independent of this invention.

Each mask 20 comprises an autonomous power source 20-1, at least one camera 20-2, communication means 20-3, of the Bluetooth® type, for short-range exchange with the unit 18, a gyroscope 20-4 and an accelerometer 20-5, and possibly other sensors such as a magnetometer and a depth sensor so as to have access to a spatial position.

Each mask 20 also comprises a transparent screen 20-6 on which can appear images and information transmitted by the unit 18 so as to allow overlaying of the real image visible in transparency and virtual images and information displayed on the screen.

The masks can be replaced by a medium of the screen type on which the overlaying is performed, but the mask provides a certain working comfort.

The device is completed by a set of n hemispherical femoral templates 22, in this case four hemispherical femoral templates 22-1 to 22-4. The inner diameters are increasing in a manner that is already known in existing ancillaries.

Figure 5:
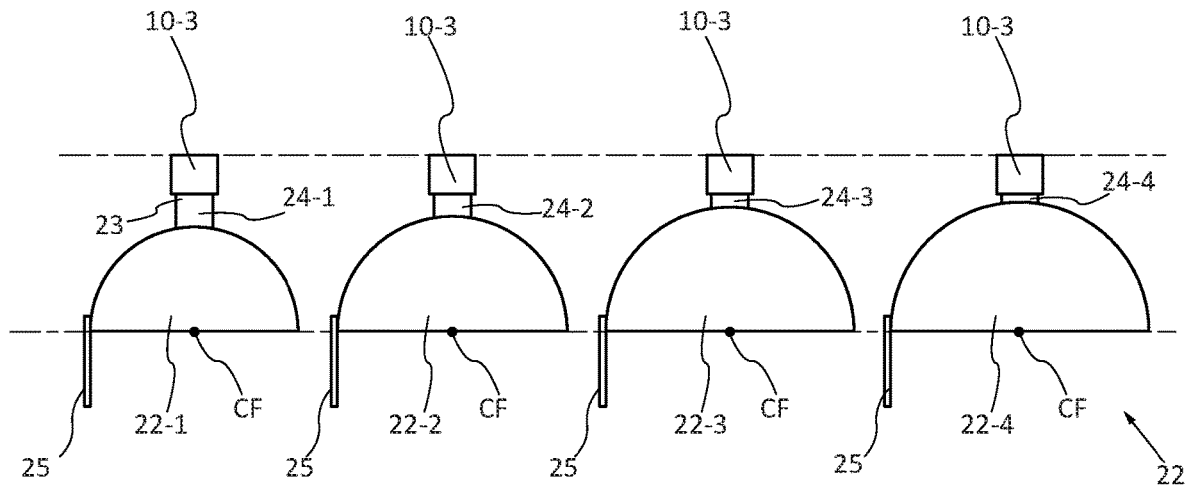
FIG. 5: third marker associated with templates of femoral heads of different diameters with risers.

These hemispherical templates correspond to different sizes of femoral heads and are intended to cap the femoral head to be replaced in one step of the method. The representation of the set is shown in detail in FIG. 5.

Each hemispherical femoral template 22 is provided with snap-fitting means 23, for example identical to the means 13-1, 13-2, intended to receive the marker 10-3. Each snap-fitting means 23 of each hemispherical femoral template is associated with a raised portion 24, in this case four extensions 24-1 to 24-4, each suitable for being interposed between the highest point of the hemisphere of the hemispherical femoral template and the marker 10-3 to be snap-fitted. Thus, the marker 10-3 is always at the same distance from the virtual center CF of the hemisphere of the hemispherical femoral template.

Of course, templates can integrate the markers directly from manufacturing.

Each template 22 is provided with an orientation rod 25 and the range may correspond to inner diameters of 36, 40, 50 and 62 mm, which are given by way of numerical example that is fully non-limiting in nature.

Figure 7:
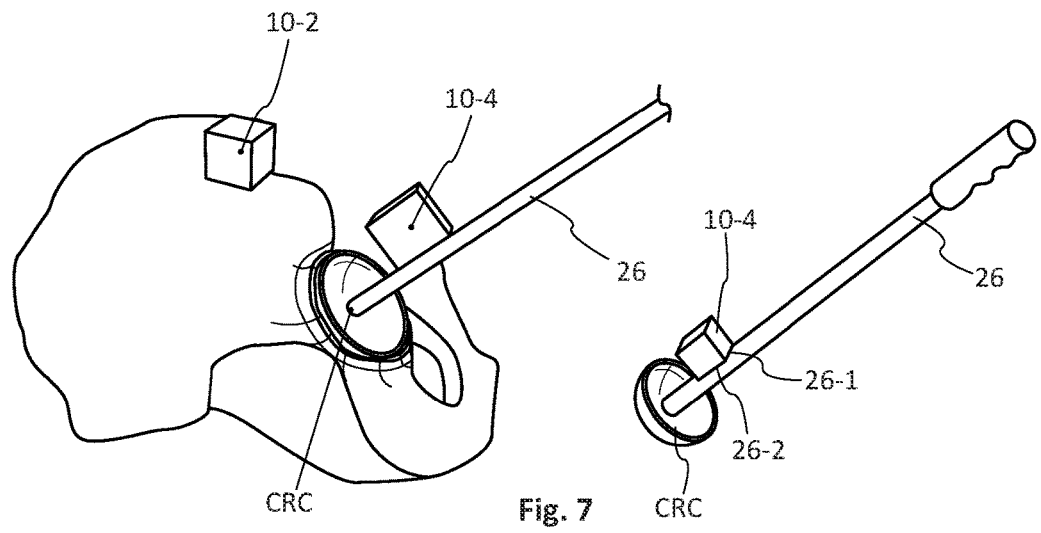
FIG. 7: recording of the initial center of rotation of the acetabulum by means of the fourth marker.

The device is also completed by trial acetabula 24, generally those of the ancillary associated with the intervention, intended to be fixed on an impactor handle 26, for example to be screwed. The impactor sleeve comprises a marker 10 carrier 26-1 with means 26-2 for snap-fitting. The carrier 26-1, in this case, receives the concerned marker 10-4, movably mounted longitudinally on the handle in order to be positioned on the basis of each acetabular template, so as to determine, in particular, the Acetabular Center of Rotation, also referred to as CRC in this document, of the patient's acetabulum intended to receive the acetabular prosthesis. This Acetabular Center of Rotation is mentioned in FIG. 7.

Figure 8:
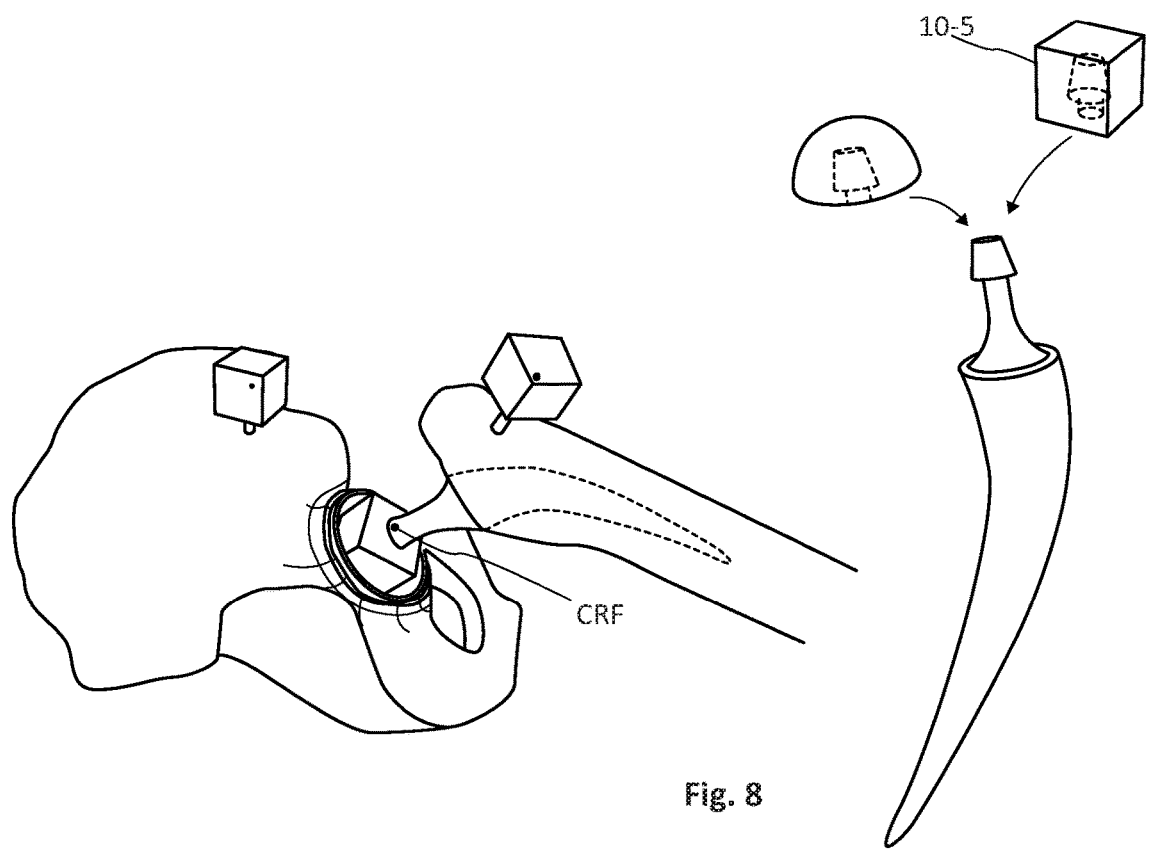
FIG. 8: implanting of the femoral stem with a fifth marker placed on the trial implant, recording and verification of the positioning of the femoral head in the acetabulum.
Figure 9:
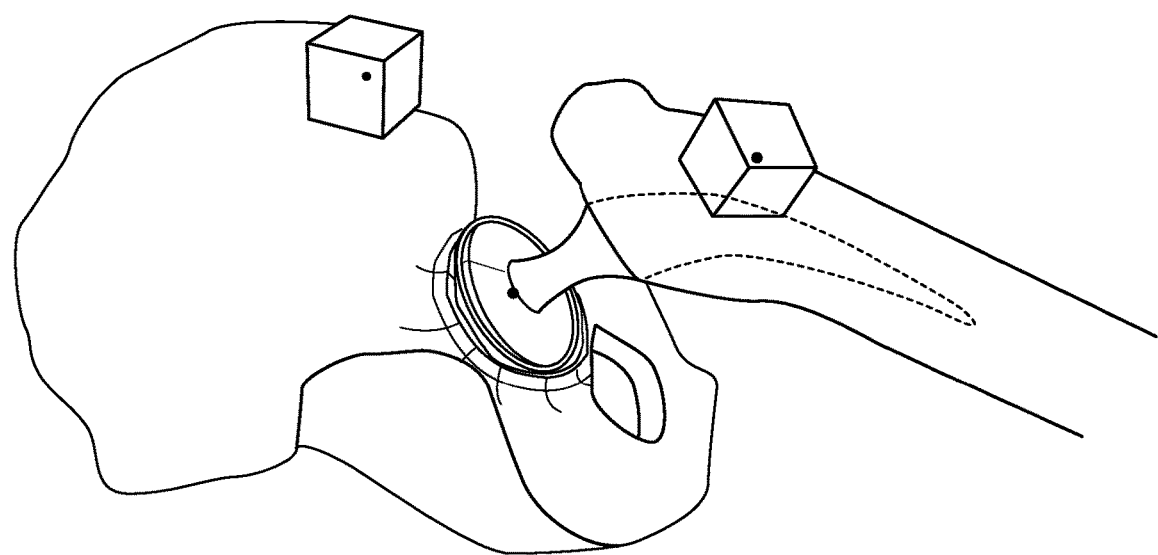
FIG. 9: mounting of the prosthetic head in place of the fifth marker.

The device also includes trial femoral stems and femoral rasps, usually those of the ancillary with femoral heads. The fifth marker 10-5 is advantageously provided with a hole like the femoral head so as to place the fifth marker on the cone of the trial femoral stem, in the stead and place of the femoral head, see FIG. 8.

Thus, the center of the fifth marker 10-5 corresponds to the center of rotation of the femoral head which will be received on the definitive femoral stem which will be implanted.

The method according to this invention comprises the sequence of steps which are now described.

The surgeon has all necessary and known ancillary operative supplies and adapted sets of prostheses; all these elements are not part of this invention.

Only the steps involving the device and the method according to this invention are described, therefore excluding all sterilization, operative and surgical procedures linked in a known manner to the operating protocol.

The surgeon fits, after incision, the surgical screw 12-1 to the femur 16 in a proximal region of the femoral head, the screw 12-1 receiving the marker 10-1, owing to the snap-fitting means 13-1. This step is shown in FIG. 2.

The femoral marker 10-1 is in a single position and constitutes a first reference position.

The surgeon fits a second surgical screw 12-2 in the pelvis 14, in a region close to the acetabulum, in such a manner as to not disturb his own actions and movements. The fitting can be performed passing through the incision or outside.

Figure 3:
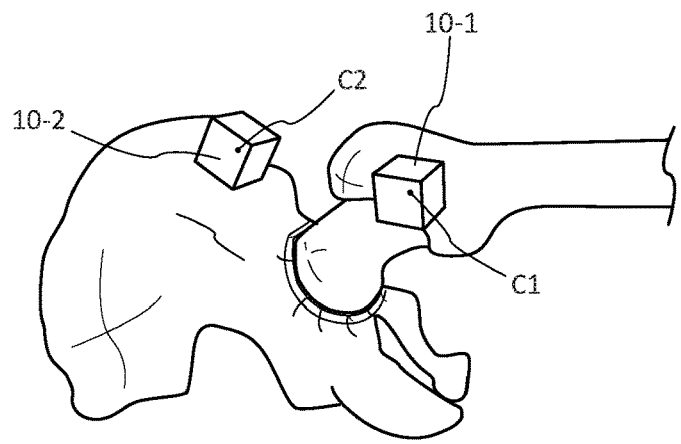
FIG. 3: fitting of a second marker on the femur and acquisition of the position of the two markers.

The second marker 10-2 is snap-fitted by the means 13-2 on the head of the second surgical screw 12-2. This step is shown in FIG. 3 which shows the two markers as implanted. It is the reference marker 10-2 which constitutes the point O of the orthonormal reference defined below in the description.

These two markers 10-1, 10-2 are recognized by the camera 20-2 of the mask 20 when the mask 20 is put into operation and worn by the surgeon. The unit 18 for acquiring the digital images and processing these images, likewise being in use, processes and stores the digital data of these two markers.

It is therefore possible to know the distance between the two centers C1 and C2 of the two markers 10-1 and 10-2. The central unit has positioned the centers C1 and C2 of these markers in 3D and these positions are accessible and viewable on the screen of the mask, but as fixed images.

Figure 4A:
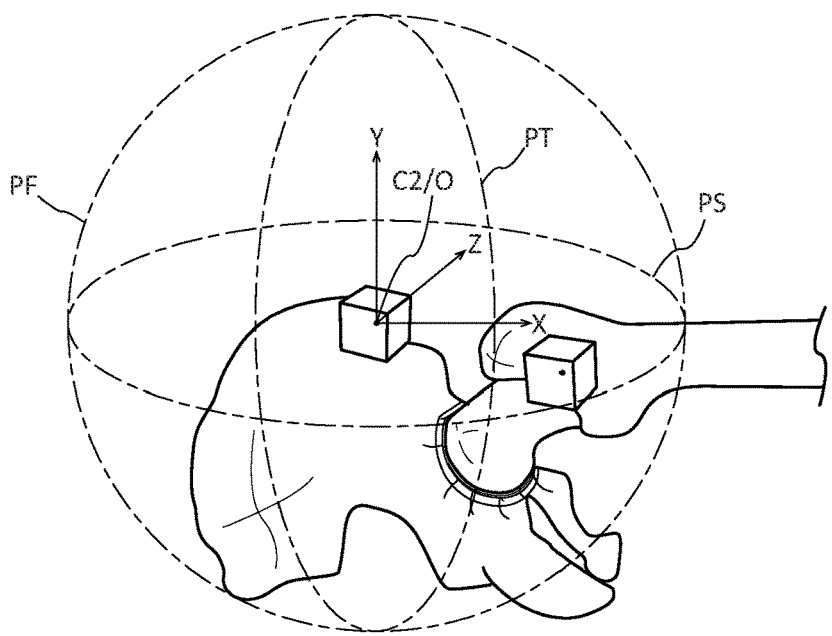
FIGS. 4A and 4B: virtual visualization of the sagittal, frontal and transversal planes, with definition of an orthonormal coordinate system.
Figure 4B:
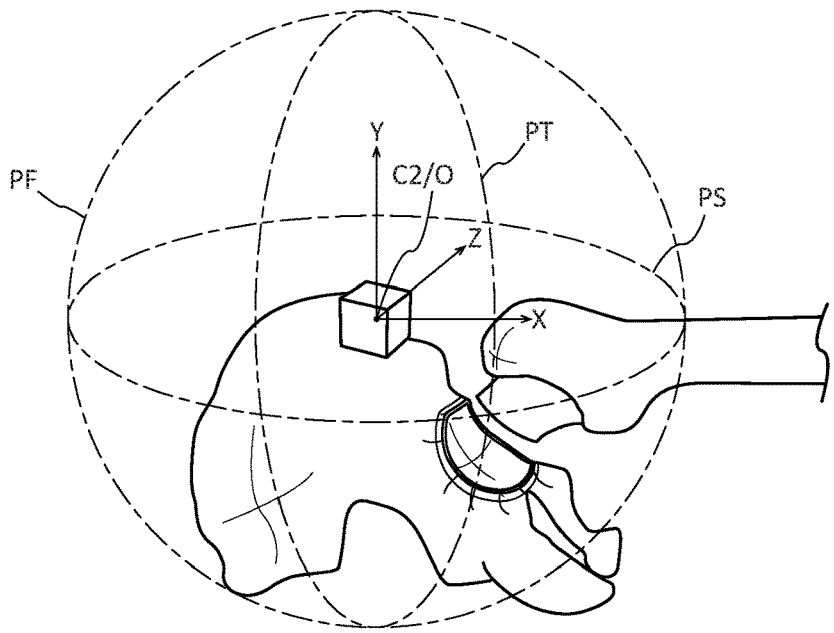

The sagittal plane PS is horizontal as indicated above and the vertical planes considered are the transversal plane PT and the frontal plane PF. The three planes are perpendicular to each other and pass through the center of the marker 10-1, see FIGS. 4A and 4B.

All other markers will be recognized with respect to this orthonormal reference point.

In this manner, the surgeon has the measurements and the positions of the different markers before the intervention.

Further reference points remain to be determined, but they require that the hip joint be dislocated, in the case of the chosen approach, in order to have access to the femoral part, including the femoral head and the acetabulum part.

Figure 6:
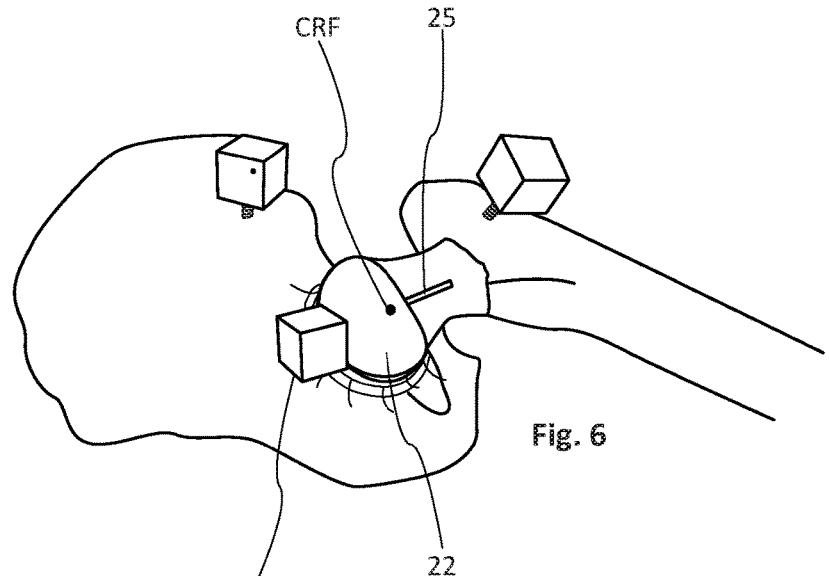
FIG. 6: trial with a femoral half-sphere and its marker and acquisition of the center of rotation of the femoral head.

The first reference is that of the femoral center of rotation, also referred to as CRF in this document, which must be determined, see FIG. 6.

For this purpose, the practitioner fits the most suitable of the hemispherical femoral templates 22-1 to 22-4 on the femoral head.

Once one of these templates is selected, it is left in place to acquire the necessary data by means of the marker 10-3, arranged on its raised portion 24.

The center of femoral rotation or CRF is then determined and recorded in 3D, since it known in relation to the template used. The software processing unit 18 also spatially records this CRF point.

It is noted that the orientation rod 25 is aligned with the axis of the neck of the femur.

This CRF point is referenced in relation to the center of the marker 10-1 to determine the distance between the femoral center of rotation CRF and the center C1 of the marker 10-1. The spatial referencing also makes it possible to determine the cervical-diaphyseal angle. The anteversion angle of the femoral neck is also recorded in order to appear virtually if necessary, for example with differential angular values between the initially recorded values and the angles recorded with the trial or final prostheses.

Once all information is acquired, the surgeon can perform the resection of the femoral head.

The surgeon can ensure the preparation of the femur to receive the femoral prosthesis determined by the measurements undertaken.

At all times, the surgeon has access to the measurements and especially the recorded virtual images of the points C1, of the initial Femoral Center of Rotation, of the angles, of the axes so as to position the prosthesis precisely without the need to measure since the values are displayed.

For this purpose, it is envisaged to equip either the tool, in this case the rasps, or the trial femoral prosthesis, with a marker 10-5 which is recognized and detects the new center of femoral rotation obtained with the prosthesis. In addition, the initial Femoral Center of Rotation CRF is also visible virtually by the surgeon so as to have the two centers of initial rotation and of the prosthesis coincide with the slightest possible deviation, or to deliberately foresee a deviation which is then indicated. This allows the practitioner to adjust by removing the trial prosthesis for reworking.

With regard to the acetabulum, the different trial prosthetic acetabula of the ancillary, having a hemispherical shape, are presented in the natural acetabulum, in order to determine its dimensions and especially to record the natural initial Acetabular Center of Rotation CRC, by means of the 10-4 marker.

The dimensional and orientation information is then determined.

The surgeon has access to the distance between the CRC and the center C2 of the second marker 10-2.

The angles of inclination and anteversion of the acetabulum are determined relative to the orthonormal reference point.

The plane of the edge of the acetabulum or equatorial plane of the hemisphere is included in a virtual disk. This disk intersects the planes with the angles of inclination and anteversion determined and recorded by means of the software data processing and recording unit 18.

The surgeon can then prepare the acetabulum, in particular, by milling in order to receive the acetabulum prosthesis according to the known and envisaged protocols.

The trial acetabular prosthesis is presented with the impactor equipped with its marker 10-4 in order to check the different dimensional and angular parameters associated with the acetabulum prosthesis versus the actual parameters measured and recorded.

The surgeon, in addition to the calculated measurements and thus the differentials that are displayed, can personally observe by overlaying the points, including the virtual center of the femoral head and another virtual equatorial disc recorded in 3D and the trial prosthesis undergoing positioning. At this stage, owing to the virtual projections on the glasses, the surgeon can verify the correspondence of the new acetabulum center of rotation obtained after the intervention with the initial natural center of rotation to determine if the positioning is acceptable. If on the contrary, the surgeon finds a medialization or lateralization of the acetabular center of rotation, it can be corrected and the surgeon knows in which direction to make the correction.

Once the preparation is finalized, the acetabulum prosthesis is then impacted and/or sealed.

The position of the acetabulum can also be checked at this stage to determine whether it has been sufficiently impacted and whether it corresponds to the recorded prosthetic center of rotation.

It is therefore possible to proceed with the reduction of the hip and fitting of the femoral prosthesis in the acetabulum prosthesis. The "prosthetic" center of rotation must be as close as possible to the recorded natural center of rotation.

It is also possible to provide a second orthonormal reference point with its center based on the marker 10-1 of the femur before the intervention.

The surgeon can then overlay the orthonormal reference point determined based on the marker 10-1 after the intervention with the orthonormal reference point that was fixed and recorded before the intervention, which helps the surgeon to position the lower limb after intervention in the exact same geometry as it was initially.

In general, the method according to this invention for assisting a surgeon fit a prosthesis between at least two bones of at least two limbs of a patient, in particular for hip, knee or shoulder arthroplasty, according to a determined orthopedic surgical protocol, comprises the sequence of the following steps:

affixing of at least one 3D marker on each of the at least two bones of the at least two limbs of the patient, virtual determination and recording of the 3D position of each marker, processing by computer means of the recorded parameters: virtual calculated points, axes and planes, surgical intervention and preparation of each bone that is to receive a prosthesis according to the determined orthopedic surgical protocol, checking the preparation of each of the at least two bones with at least one marker attached to a trial prosthesis and/or to a preparation tool, by continuously overlaying each point, straight line and real virtual plane recorded on the bone of the patient with the corresponding points of the prosthesis, placement of each determined prosthesis on each of the at least two bones, and calculation of the final implant parameters in relation to the recorded natural parameters.

Such a method and such a device can be implemented for knee or shoulder prostheses by simple transposition.

The device uses markers of the 3D QR Code type but a total virtual recognition can also be considered.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for assisting a surgeon fit a prosthesis between at least two bones of a patient for hip, knee or shoulder arthroplasty, according to a determined orthopedic surgical protocol comprising at least the following steps, which as such have been excluded from the method of assisting the fitting of said prosthesis:
  intervention to allow access to the bones concerned,
  surgical intervention and preparation of each bone that is to receive a prosthesis according to said determined orthopedic surgical protocol,
  checking the position of the bones concerned,
  placement of each determined prosthesis on each of the at least two bones, the method comprising a sequence of the following steps:
  affixing at least one 3D marker on each of the at least two bones of at least two limbs of the patient, each 3D marker being a cube with each face being identified by a QR code,
  virtually determining and recording a 3D position of each 3D marker,
  processing, by a computer, of recorded natural parameters: virtual calculated points, axes and planes,
  checking the preparation of each of the at least two bones with the 3D marker attached to the bones, by continuously overlaying each point, straight line and real virtual plane recorded on the bone of the patient with corresponding points of the prosthesis,
  calculating final implant parameters in relation to the recorded natural parameters,
  displaying the recorded and calculated virtual parameters directly on a transparent screen so as to be overlaid on each limb and each prosthesis and provide an augmented realty display in which the virtual parameters are virtually projected on each limb and each prosthesis,
  the transparent screen mounted on a pair of glasses to be worn by said surgeon.

2. A device for implementing a method for assisting a surgeon fit a prosthesis between at least two bones of a patient for hip, knee or shoulder arthroplasty, comprising:
  at least three 3D markers, including two 3D markers, each configured to be affixed to one of the at least two bones, each 3D marker being a cube with each face being identified by a QR code, each 3D marker associated with a surgical screw configured to lock the respective 3D marker in a single position,
  a data processing and recording unit,
  a mask comprising an autonomous energy source,
  a camera,
  a communication device configured to provide short-range exchange with said data processing and recording unit,
  a transparent screen for displaying images and information transmitted by said data processing and recording unit so as to provide overlaying of a real image visible in transparency and virtual images and information displayed on the screen as an augmented realty display,
  wherein the camera is arranged, when the mask is in use, to recognize the 3D markers,
wherein the data processing and recording unit is configured to determine and record a 3D position of the centers of each 3D marker attached to the bones and to position and freeze, on the transparent screen, the centers of the 3D markers, the center of one of the 3D markers constituting the origin of an orthonormal frame of reference.

3. The device according to claim 2, further comprising a gyroscope and an accelerometer, both associated with the mask so as to have access to a spatial position.

4. The device according to claim 3, further comprising a magnetometer and a depth sensor.

5. The device according to claim 2, wherein the transparent screen is mounted on a pair of glasses to be worn by said surgeon.

* * * * *